United States Patent
Nelson et al.

(10) Patent No.: US 10,639,333 B2
(45) Date of Patent: *May 5, 2020

(54) PROCESS FOR REMOVING GROWTH FACTORS FROM PLATELETS

(71) Applicant: PGFX Patent Holdings, LLC, West Monroe, LA (US)

(72) Inventors: Gary H. Nelson, Fort Myers, FL (US); Ryan N Brandt, Fort Myers, FL (US); Clark Galen, Sarasota, FL (US); John Kiwczak, Sarasota, FL (US)

(*) Notice: Subject to any disclaimer, the term of this patent is extended or adjusted under 35 U.S.C. 154(b) by 313 days.

This patent is subject to a terminal disclaimer.

(21) Appl. No.: 15/700,084

(22) Filed: Sep. 9, 2017

(65) Prior Publication Data

US 2018/0133256 A1     May 17, 2018

Related U.S. Application Data

(60) Division of application No. 14/544,411, filed on Jan. 2, 2015, now Pat. No. 9,757,418, which is a continuation-in-part of application No. 14/120,487, filed on May 23, 2014, now Pat. No. 9,511,118, which is a division of application No. 12/459,911, filed on Jul. 9, 2009, now Pat. No. 8,734,854.

(51) Int. Cl.
| | |
|---|---|
| *A61K 35/19* | (2015.01) |
| *A61L 27/36* | (2006.01) |
| *A61L 27/54* | (2006.01) |
| *A61K 45/06* | (2006.01) |
| *A61K 38/18* | (2006.01) |
| *C12N 1/06* | (2006.01) |
| *A61K 35/16* | (2015.01) |
| *C07K 14/475* | (2006.01) |
| *A61K 47/42* | (2017.01) |

(52) U.S. Cl.
CPC ............ *A61K 35/19* (2013.01); *A61K 35/16* (2013.01); *A61K 38/18* (2013.01); *A61K 38/1808* (2013.01); *A61K 38/1816* (2013.01); *A61K 38/1825* (2013.01); *A61K 38/1841* (2013.01); *A61K 38/1858* (2013.01); *A61K 45/06* (2013.01); *A61K 47/42* (2013.01); *A61L 27/3616* (2013.01); *A61L 27/54* (2013.01); *C07K 14/475* (2013.01); *C12N 1/066* (2013.01); *A61L 2300/252* (2013.01); *A61L 2300/256* (2013.01); *A61L 2300/64* (2013.01); *A61L 2430/00* (2013.01)

(58) Field of Classification Search
None
See application file for complete search history.

(56) References Cited

U.S. PATENT DOCUMENTS

| 3,375,824 A | 4/1968 | Krakauer et al. |
| 2006/0004189 A1 | 1/2006 | Gandy |

FOREIGN PATENT DOCUMENTS

| EP | 0308238 | 3/1989 |

OTHER PUBLICATIONS

James P. Maloney et al. "In Vitro Release of Vascular Endothelial Growth Factor During Platelet Aggregation" Am J Physiol Heart Circ Physiol 275:H1054-H1061, 1998.

Murayma et al. "Ex Divo Human Platelet Aggregation Induced E W Decompression During Barometric Pressure Hydrostatic and Hydrodynamic (Bernoulli) Effect" Thrombosis Research 33 477-485, 1985.

Seppae et al. "Platelet-Derived Growth Factor Is Chemotactic for Fibroblasts" J Cell Biol. Fed. 1982; 92 (2): 584-8.

Richter et al. "Composition of the peptide fraction in human blood plasma: database of circulating human peptides". Journal of Chromatography B, 726 (1999) 25-35.

*Primary Examiner* — Thane Underdahl
(74) *Attorney, Agent, or Firm* — Price & Adams, P.C.

(57) ABSTRACT

In vitro and in vivo application of sub-atmospheric, negative pressure on growth factor starting material, such as whole blood, extracts growth factors from the platelet granules of the growth factor starting material in a non-destructive medium without activating the clotting process. The extracted growth factors are released into a growth factor composition containing blood plasma, extracellular fluid or interstitial fluid depending upon the type and location of the growth factor starting material. The growth factors have a weight of about 70-76 kDaltons and are applied in either a filtered or unfiltered state topically to the area of a surface wound to effect healing. The extracted growth factors are also injected into soft tissue, such as a torn tendon, to promote tissue growth and healing. The growth factors are released in one method from a patient's own blood. In another method the growth factors are released from a whole blood source and freeze dried by lyophilization. Then at a later date, the freeze-dried product is reconstituted by normal saline for treatment of a patient's wound, for use in a surgical procedure, or for tissue regeneration.

13 Claims, 6 Drawing Sheets

PROCESS FOR REMOVING GROWTH FACTORS FROM PLATELETS

CROSS-REFERENCE TO RELATED APPLICATIONS

This application is a division of U.S. application Ser. No. 14/544,411 "Process for Removing Growth Factors from Platelets" filed on Jan. 2, 2015 which is a continuation in part of U.S. application Ser. No. 14/120,487 filed on May 23, 2014, now U.S. Pat. No. 9,511,118, which is a division of U.S. application Ser. No. 12/459,911 filed Jul. 9, 2009, now U.S. Pat. No. 8,734,854.

BACKGROUND OF THE INVENTION

1. Field of the Invention

The invention relates to a process for extracting growth factors from growth factor starting material and other cellular components from platelets, platelet rich plasma, and whole blood and, more particularly, to a wound healing and tissue regenerative composition of growth factors and cellular components released from intracellular granules and cellular structures bound by mammalian platelet membranes for use in wound healing and other therapeutic and biomedical uses to repair, regenerate, restore and provide bioscaffold components to promote and support living cells and tissues and for the purpose of stabilizing or reversing impairment of the normal state of the living animal body or one of its parts whose function has been interrupted or performance of the vital functions compromised by injury, disease, or aging.

2. Description of the Prior Art

The practice of using activated autologous platelets as a treatment in a number of medical and surgical procedures is known, including but not limited to oral and maxillofacial surgery, orthopedic surgery, cosmetic and reconstructive surgery, chronic tissue repair, sports medicine injuries, neurosurgery, cardiovascular surgery, podiatry, hair transplant surgery, immune mediated hair loss, medical research, tissue engineering, and non-surgical cellular therapy. U.S. Pat. Nos. 4,957,742 and 6,649,072 disclose wound healing compositions that include platelet rich plasma (PRP) which prior to use is activated by thrombin to release growth factors from the alpha granules of the platelets.

Extracting therapeutic levels of platelets has been a technical challenge requiring trained cardiovascular perfusionists to operate the equipment originally designed for the production of platelet rich plasma. The clinical practitioner now has access to more simplified equipment that allow processing of PRP with smaller amounts of whole blood in a shorter amount of time. Venous access, clinical expertise, and cost are still challenges that have limited the widespread use of this process throughout the world. Moreover from a commercial standpoint, wound-healing compositions that include platelets must meet costly FDA guidelines applicable to blood products.

Platelet rich plasma (PRP) compositions are being utilized for both human and veterinary applications. PRP formulations may or may not include leucocytes (white blood cells) and are referred to leucocyte-rich PRP or leucocyte-poor PRP. As the knowledge of growth factors expands, a greater understanding of specific growth factors has helped to define their roles with greater precision. In general, while platelets influence anabolic signaling to promote the proliferative and regenerative phases of the healing cascade, leucocytes contain cytokines, a class of growth factors with catabolic activity supportive of an inflammatory response. Thus, a PRP preparation or a growth factor composition can be tailored to the desired anabolic or catabolic activities through selective inclusion or exclusion of leucocytes.

Growth factors are responsible for the wound healing process, as described above. Platelets function as carriers for the growth factors. Growth factors are polypeptides produced by the tissue on which they act. They regulate differentiation, proliferation, migration, and metabolism in target cells, regulating the synthesis of specific adhesion molecules that control cell-cell and cell-substrate interactions. Each GF can have either one or several essential functions for a specific cell, depending on the particular circumstances of the cell environment.

The most widely studied growth factors in relation to tissue proliferation and repair include: bone morphogenetic proteins (BMPs) (eg, BMP-1, BMP-2, and BMP-3); PDGF; insulin-like growth factor (IGFs) (eg, IGF-I and IGF-II); TGFs, especially TGF-β; fibroblast growth factors (FGFs) (ie, acid-FGF and basic-FGF); granulocyte macrophage colony stimulating factor; epidermal growth factor; and VEGF. An important role in repair processes, specifically in the inflammation stages, is also played by cytokines produced by white blood cells, including the interleukins (Its) IL-1, IL-3, IL-6, and IL-8. All of these growth factors and cytokines act to a greater or lesser extent during the different stages of wound healing which includes tissue necrosis resolution, cell regeneration, cell proliferation and migration, extracellular matrix synthesis, epithelialization, and remodeling.

There is need for an efficient process for extracting and isolating growth factors and platelet granule contents from the platelets contained in plasma for subsequent use in wound healing and for a multitude of bioactive processes supportive of living tissue(s) associated with in vivo or in vitro processes. Preferably, the final product would be a growth factor composition with minimal to no cellular debris.

It is further desirable to prepare a wound healing product, expanded to include processes as described above, that can be subjected to conventional preservation procedures, such as lyophilization, freeze drying, and cryopreservation in a process that does not destroy the growth factors nor the functionality of the growth factor composition. In this manner the shelf life of the product(s) would be significantly prolonged.

In addition to local hemostasis at sites of vascular injury, platelets contain an abundance of growth factors and cytokines that are pivotal in soft tissue healing and bone mineralization. An increased awareness of platelets and their role in the healing process has led to the concept of therapeutic applications.

The preparation of PRP is still dependent on whole platelets, centrifugation or gravity flow or filtration techniques with the exception of cytokine rich plasma (CRP), as discussed in U.S. Pat. No. 8,734,854. During the early years of development, the terminology cytokine rich plasma represented both growth factors and cytokines. More recently growth factors have come to represent positive tissue repair influences and regeneration while cytokines are associated with inflammation, pain, and cleaning up of wounds.

It should be understood that CRP composes both classification types but may be better thought of as complex or complete rich plasma. CRP is unique to PRP in both composition and concentration. Although similar in many ways, the differences are relevant. Intact platelets are common to all forms of PRP. CRP is developed under the influence of sub-atmospheric pressures. Growth factors, cytokines and other intracellular proteins and biochemical components normally released by agonists are extracted from their intracellular positions without the use of agonists. The result: CRP is overwhelmingly acellular.

Production of PRP inherently results in less than 100% of the original content of whole blood cell types of interest. Production of CRP may be derived from 100% of the cellular content of whole blood. Whole blood or various blood cell components, specifically platelets and or white blood cells, are subjected to sub-atmospheric pressures. Maximal levels of each sample's cellular proteins are separated from their intracellular location and released to the extracellular (extracorporeal) fluid environment. Additionally, assays of the sub-atmospheric treated blood led to findings of two peptides not previously recognized and is disclosed in U.S. Pat. No. 8,734,854.

Processing the blood components after being exposed to controlled sub-atmospheric pressure allows for separation of CRP from red blood cells, ghost cells and cell debris resulting in an acellular content. The CRP can then be directly applied to a patient; filtered to remove water thereby concentrating the product into a smaller volume for application in areas where smaller volumes are more efficacious, such as within the confined space of joint, or stored by a unique lyophilization process. Discovered by accident, this specific method of lyophilization preserves biofunctionality, the ability to express bioactive properties, of the CRP components without the addition of fixatives. The latter process remains a trade secret to the inventors.

It has long been the goal to finding a means of preserving or extending the functional longevity of the platelet. Utilizing the concept of negative (sub-atmospheric) pressure, living tissues composed of whole blood and portions thereof were subjected to controlled levels of negative pressures. Under the appropriate range of negative pressure, the blood cell maintains its integrity while undergoing expansion. Too much negative pressure and the cell tears apart. Not enough negative pressure and the cell will not react. With the appropriate degree of negative pressure applied over a defined timeline, the cell expands reducing internal pressures such that particulate matter contained with intracellular alpha, delta (dense) or lambda granules find a pathway of least resistance as they are freed from their confines of the expanding granule membrane. These intra-granule particles are drawn to the lower pressure outside the cell membrane and into the extracellular environment. The contents of the granules are emptied without destroying the integrity of the cell membranes.

The natural life expectancy of a platelet and its granular contents are limited to days using standard blood banking processes. Platelets are cytoplasmic fragments of megakaryocytes lacking nuclei but containing organelles and structures such as mitochondria, microtubules, and three main types of granules. Due to ongoing mitochondrial activity, and mRNA synthesis of proteins, this meets the description of a living cell. These short-lived cells or cell fragments, whichever one prefers to view them as, have undergone extensive research in order to come up with a reliable means of preservation with retention of normal bioactive potential. For this purpose, platelets will be viewed as cells.

Platelets reside intravascularly. Therefore, any tissue containing a vascular supply will have the same platelet content. The normal concentration of platelets in blood is approximately 140,000 to 400,000 platelets/mm3. These remain in the circulation for about 10 days. Therefore any disruption in one's ability to replace platelets would have rapid and profound effects in the event of a sustained trauma. After tissue injury, platelets are among the first cells to appear and remain in the vicinity of the wound.

The benefits of controlling the collection of and when desirable, the storage of this limited resource, to extend the useful function of a platelet or its contents, would have significant impact on the practice of medicine as it applies to wound healing, regenerative medicine, and other therapeutic and biomedical uses for the purpose of stabilizing or reversing impairment of the normal state of the living animal body or one of its parts whose function has been interrupted or performance of the vital functions compromised by injury, disease, or aging.

Historically, the main purpose of preserving the platelet pertains to correcting bleeding disorders stemming from deficiencies in platelet numbers or platelet function. Advancing technologies have allowed for a growing body of evidence to reveal the critical and diverse role the platelet in the wound healing cascade that includes the steps of hemostasis (clotting), inflammation, proliferation, and regeneration (remodeling) of tissues. Platelets regulate and modulate the rate of tissue repair by releasing biochemical messages, growth factors, that can affect the cell from which it originates (autocrine), or influence local cell activity (paracrine) or distant (endocrine) cell activity. This call to action influences multi-cell activity as well as the migration of healing components to the site of injury.

Over 1200 types of proteins have been identified on or within a platelet. There are approximately 50 to 80 alpha granules per platelet containing greater than 400 different bioactive proteins whose complex interactions in the healing cascade are not yet fully clarified. Dense bodies or Delta granules (250-300 nm) contain ATP, proaggregatory factors such as adenosine 5'-diphosphate (ADP), calcium, and 5-hydroxytryptamine (serotonin), pyrophosphate, histamine and other factors which promote adhesion of platelets and cause vasoconstriction. Lambda granules (175-250 nm) contain lysosomal, proteases, lipases, nucleases and polysaccharidases. These bioactive enzymes function to remove infectious agents and cellular debris.

It should be understood that PRP is more than just platelets and that it contains many bioactive factors that act in anabolic, catabolic, proinflammatory, and anti-inflammatory pathways. Some components are also involved in the modulation of the immune response. The precise combination and concentration of platelets, leukocytes, and other plasma components best for musculoskeletal healing are not presently known, and clinicians should be aware that the effects of PRP are not solely based on platelet concentration. A maximal efficacious concentration beyond which the platelet concentration will provide no further clinical benefits likely exists. Although the effects of many of the proteins in PRP on musculoskeletal tissues are still unknown, they likely contribute to the biologic healing process. Finally, it is imperative for individuals involved in clinical study design and all clinicians to take into consideration diurnal variation in platelet count and that, simply, generation of PRP will fail in some patients in some instances.

Activation of a platelet by an agonist, such as thrombin, collagen, or other agonist known in the art, leads to the differential release of granule material from within the platelet. Such granulation activation (differential degranulation) results in the specific and sequential release of groups of growth factors and other granular contents over time.

Physical agonists such as rapid cooling and freezing temperatures as used in standard lyophilization, cryopreservation, and freeze drying processes result in a percentage of platelet destruction and a significant loss of bioactivity rendering them less potent. The appropriate application of sub-atmospheric pressure results in a rapid and thorough release of granular contents with retention of bioactivity.

The platelet cytoplasm contains two distinct pathways: first a closed dense tubular system which does not open to the cell membrane and second an open cannicular system which appears to be an invagination of the outer cell membrane and does open to the cell membrane and through which platelet granular contents are dispersed when activated. Where the dense tubular system lies adjacent to the open cannicular system, transfer of proteins across membranes will occur. During the unconventional application of a sub-atmospheric pressure without the use of natural or known platelet activators, findings support that negative pressures assist in the nonspecific extraction (release) and discharge of granular contents into the dense tubular system and or cannicular system of the platelet from which growth factors are released beyond the cell membrane to the extracellular (extracorporeal) environment. In effect, a rapid and complete, non-differential or nonspecific release of granular material results from a sufficient application of sub-atmospheric pressure.

Membranous pseudopod formation is discussed at length in the medical literature. Natural or agonist induced activated platelets undergo pseudopod formation. Studies are lacking as to whether or not sub-atmospheric pressure will induce pseudopod formation but it is hypothesized that it will not occur with rapidly applied negative pressure. Rather the entire platelet cell will expand more uniformly.

Human platelet granules degranulate via the intracellular caninicular system and dense tubular system. Equine and bovine platelet granules have been shown to release growth factors directly from the cellular membrane. Canine platelet degranulation appears to vary between cell membrane and cannicular system. Various forms of disease have been studied that have an affect on the platelet degranulation process.

When applied to existing wounds, growth factors are known to attract more platelets (proaggregatory factors), macrophages, regenerative cells such as mesenchymal stem cells and osteoblasts, and increase the rate of collagen laydown, vascular ingrowth, fibroblast proliferation and overall healing. The release of a protein known as platelet-derived growth factor (PDGF) serves as a chemotactic signal for monocytes, neutrophils and fibroblasts, which then move into the wound to begin the inflammatory stage of the healing process. During this time, monocytes secrete a number of factors, including PDGF and transforming growth factor-beta 1 (TGF-β1) also found in platelets. In this manner fibroblasts are activated to begin the repair or regenerative stage of the healing process. Subsequently, wound healing continues through the process of collagen remodeling within the wound.

Platelet rich plasma compositions are being utilized for both human and veterinary applications. PRP formulations may or may not include leucocytes (white blood cells) and are referred to leucocyte-rich PRP or leucocyte-poor PRP. As the knowledge of growth factors expands, a greater understanding of specific growth factors has helped to define their roles with greater precision. In general, while platelets influence anabolic signaling to promote the proliferative and regenerative phases of the healing cascade, leucocytes contain cytokines, a class of growth factors with catabolic activity supportive of an inflammatory response to help resist infection and remove cellular and tissue debris. Thus, a PRP preparation or a growth factor composition can be tailored to the desired anabolic or catabolic activities through selective inclusion or exclusion of leucocytes.

Growth factors are responsible for the wound healing process, as described above. Platelets function as carriers for the growth factors. This further understanding is clearly recognized and included with use of the terminology "growth factor composition" which is understood to include the contents of platelet alpha, dense, and lambda granules that contain over 400 different bioactive proteins and biochemicals whose complex interactions in the healing process are not yet fully clarified as well as components of the extracellular fluid or plasma. Therefore, there is a desire for an efficient process for extracting and isolating growth factors and when appropriate, additional bio-substances, from the platelets and the blood, plasma, or tissue(s) containing the platelets at the time of application of the sub-atmospheric pressure for subsequent use in wound healing and for a multitude of bioactive processes supportive of living tissue associated with in vivo or in vitro processes. The use of a natural growth factor composition as part of a supportive medium or bioscaffold to produce whole organs or tissues in vitro has significant implications. Preferably, the final product shall be free of other selective components that are typically found in conventional platelet enriched wound healing products, namely whole platelets, ghost platelets, white blood cells, red blood cells, bacteria, and other cellular debris.

There is further benefit to preparing naturally derived wound healing products that can be subjected to conventional preservations, such as lyophilization, freeze drying, and cryopreservation in a process that does not destroy the growth factors nor the functionality of the growth factor composition. In this manner the shelf life of the product(s) would be significantly prolonged.

Therefore, there is a need for a process for isolating and extracting growth factors in a non-destructive manner from platelets. The resulting composition may selectively contain other platelet and if desired platelet rich plasma components or, may or may not be substantially free of other components, such as whole platelets, ghost platelets, white blood cells, red blood cells and bacteria, and can be used fresh for immediate use or lyophilized for delayed use into a shelf-stable, non-refrigerated product for subsequent use.

SUMMARY OF THE INVENTION

In accordance with the present invention there is provided a process for obtaining growth factors that includes the steps of providing a preselected volume of unfrozen growth factor starting material wherein the unfrozen growth factor starting material contains platelets obtained from the tissue of a subject. A preselected sub-atmospheric pressure is applied to the unfrozen growth factor starting material to extract growth factors from the platelet granules of the unfrozen growth factor starting material without activating the clotting process within the growth factor starting material. The extracted growth factors are released from the cellular structure of the growth factor starting material into extracellular fluid to provide an extracellular growth factor composition containing the extracted growth factors. The extracted growth factors are collected for mixture with a nondestructive medium without dehydrating the growth factor starting material. The nondestructive medium contains a therapeutically effective amount of growth factors for creating a positive reaction on living tissue.

Further, in accordance with the present invention there is provided a wound healing and tissue regenerative composition that includes unfrozen growth factor starting material including platelet granules obtained from the tissue of a subject. The growth factors are extracted from the platelet granules of the unfrozen growth factor starting material. The extracted growth factors remain in an inactivated state. The extracted growth factors are substantially free of cellular structure of the growth factor starting material. The extracted growth factors are mixed with a nondestructive medium in a bioactive state to generate a positive reaction on living tissue to enhance tissue repair and or growth.

Additionally, the present invention is directed to a process for obtaining growth factors that includes the steps of providing a preselected in vivo site of growth factor starting material containing platelets obtained from the tissue of a subject. A preselected sub-atmospheric pressure is applied to the growth factor starting material to extract growth factors from the platelet granules of the growth factor starting material over a preselected period of time without activating the clotting process within the growth factor starting material. The concentration of available platelet free growth factors is raised within the growth factor starting material to a magnitude of extracellular physiological concentration exceeding the magnitude normally found in extracellular physiological concentration. The extracellular physiological concentration of platelet free growth factors upon application promotes an acceleration of the healing cascade.

Further, the present invention is directed to a process for producing a therapeutically and regeneratively effective bio-functional agent that includes the steps of extracting growth factors from platelets of growth factor starting material derived from the tissue of a subject without activating the growth factors and with the growth factors remaining in a natural state. A growth factor composition is produced including growth factors extracted from platelets. The growth factor composition is separated from the growth factor starting material. The growth factor composition is collected and applied as a catalyst in the formation of an extracellular tissue matrix for creating a positive reaction on living tissue.

DESCRIPTION OF THE PREFERRED EMBODIMENTS

Figure 1:
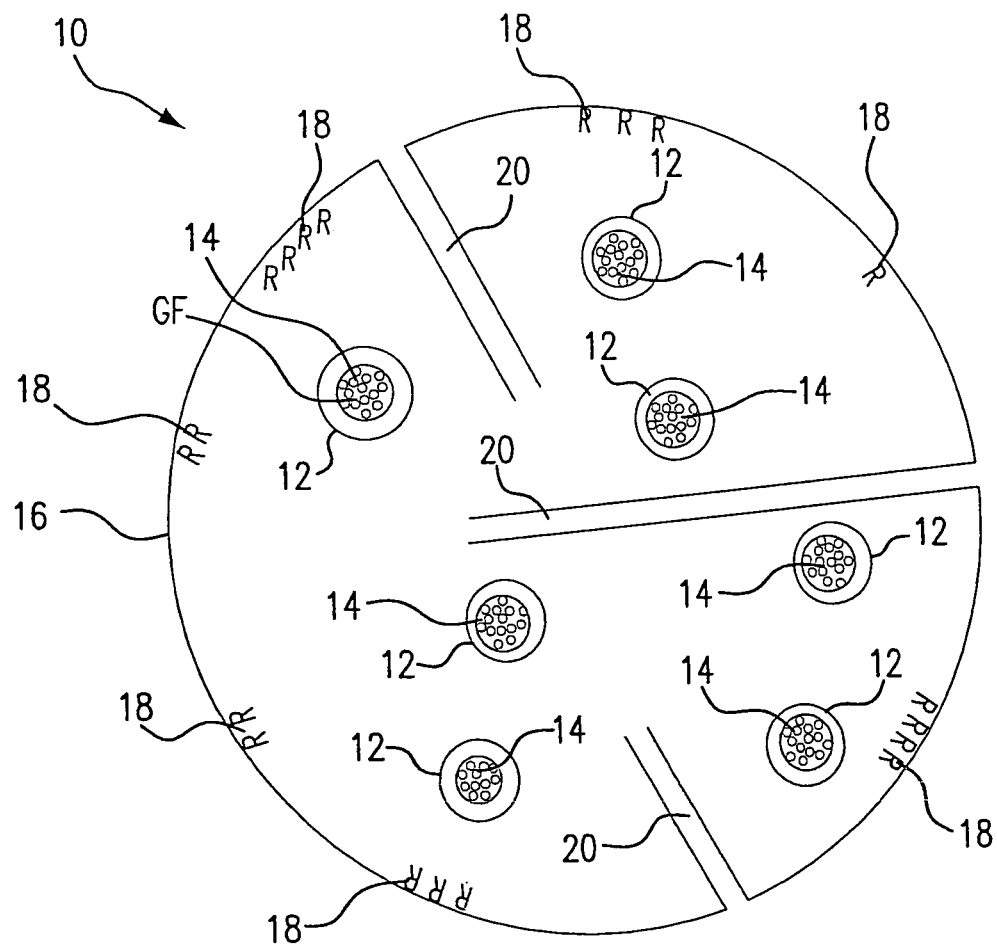
FIG. 1 is a schematic diagram of a resting platelet circulating in blood plasma prior to activation by an agonist.

The process of the present invention removes growth factors from platelets for subsequent use in wound healing and tissue regenerative processes, either alone or in combination with other healing components present in plasma or other growth factor (cytokine) bearing cells such as leucocytes. In accordance with the prior art processes, platelet concentrated plasma products are prepared through multi-step processes and then subsequently activated with one or more known activation processes, such as thrombin or collagen, to release the growth factors and other platelet granule components from the platelets' alpha granules. In contrast, the process of the present invention allows for the separation of growth factors from normal and concentrated levels of platelets without the need to use activators (agonists), such as thrombin or collagen. Consequently, with the present invention platelet degranulation and growth factor release is carried out without the occurrence of clotting. As a result, a higher yield of growth factors is obtained. Further, adhesion molecules typically consumed in formation of a clot are harvested for later use. The released growth factors remain inactivated so that they retain bioactivity and bio-messenger capacity separate from or in the presence of fibrinogen, fibronectin, and vitronectin in a nondestructive medium, such as plasma, sterile water, saline, and the like. The bio-messenger capacity of the released growth factors results in signaling a change or response in the behavior of a living cell, including the cell of origin. In a bioactive state the released growth factors have a positive reaction on living tissue, which in one example provides enhanced wound healing. The growth factors and adhesion molecules may be lyophilized, for example, to prepare a freeze-dried product with a shelf life much longer than non-lyophilized platelet products.

As used herein, the term growth factors refers to any material or materials having a positive reaction on living tissues, such as promoting the growth of tissues. Exemplary growth factors include, but are not limited to, platelet-derived epidermal growth factor (PDEGF), platelet factor 4 (PF 4), transforming growth factor beta (TGF-β), acidic fibroblast growth factor (FGF-A), basic fibroblast growth factor (FGF-B), transforming growth factor A (TGF A), insulin-like growth factors 1 and 2 (IGF-1 and IGF-2), B thromboglobulin-related proteins (BTG), thrombospondin (TSP), fibronectin, von Willibrand's factor (vWF), fibropeptide A, fibrinogen, albumin, plasminogen activator inhibitor 1 (PAI-1), osteonectin, regulated upon activation normal T cell expressed and presumably secreted (RANTES), gro-A, vitronectin, fibrin D-dimer, factor V, antithrombin III, immunoglobulin-G (IgG), immunoglobulin-M (IgM), immunoglobulin A (IgA), a2-macroglobulin, aniogenin, Fg-D, elastase, keratinocyte growth factor (KGF), epidermal growth factor (EGF), tumor necrosis factor (TNF), fibroblast growth factor (FGF) and interleukin-1 (IL-1), Keratinocyte Growth Factor-2 (KGF-2) and combinations thereof. One of the important characteristics common to the above listed growth factors is that each substance is known as or believed to have a positive reaction on living tissue, known as bioactivity, (anabolic) to enhance cell or tissue growth.

In the context of the healing cascade having positive effects on living tissues, the inflammatory stage has distinct aspects associated with it in which tissues are prepared for a healthy recovery but in order to achieve this they must first go through a catabolic or clean up phase to eliminate devitalized cells and microbial and foreign body contaminants. Pain is associated with inflammation. Cytokines help to regulate the pain response. The presence and or absence of specific interleukins determine the degree of pain experienced during the inflammatory phase of healing. Chronic pain such as that experienced in osteoarthritis occurs from prolonged cellular trauma where wear and tear on the affected tissues never allow for complete healing. Therapies utilizing PRP, platelet and leucocyte derived interleukins have been recognized. This remains one exception to positive aspects of the healing cascade and provides a platform for the use of growth factor compositions to overcome the pain response associated with chronic osteoarthritis.

Growth factor starting material as used herein refers to any source of unfrozen animal tissue containing one or more growth factor components, such as platelets, PRP, whole blood, bone marrow, umbilical cord fluid, adipose tissue, vascular tissue, and combinations thereof. All embryonic derived tissues of mesodermal, endodermal and ectodermal origin are sources of growth factor starting material. For example, adipose tissue is composed of fat cells called adipocytes and vascular components. The vascular components are composed of blood vessels containing cells with growth factor components. Therefore, adipose tissue is a source of growth factors. Any tissue or organ with a blood supply contains growth factor starting material.

FIG. 1 schematically illustrates an inactivated platelet or resting platelet generally designated by the numeral 10. The platelet 10 contains alpha granules 12 that are filled with growth factors 14 that are released from the alpha granules and platelet 10 in accordance with the present invention. The platelet circulates in the blood plasma ready to respond if activated by one or more agonists. A membrane 16 surrounds the platelet and includes receptors 18 positioned at the membrane 16. The platelet 10 includes an intracellular system within the membrane 16 and an extracellular system external of the membrane 16. The extracellular system outside the platelet includes a fluid in which the platelet circulates. The intracellular system includes a dense tubular system (not shown) and a cannicular system 20. The dense tubular system is not open to the environment external of the platelet; however, as shown in FIG. 1, the cannicular system 20 is open to the environment external to the platelet 10.

Figure 2:
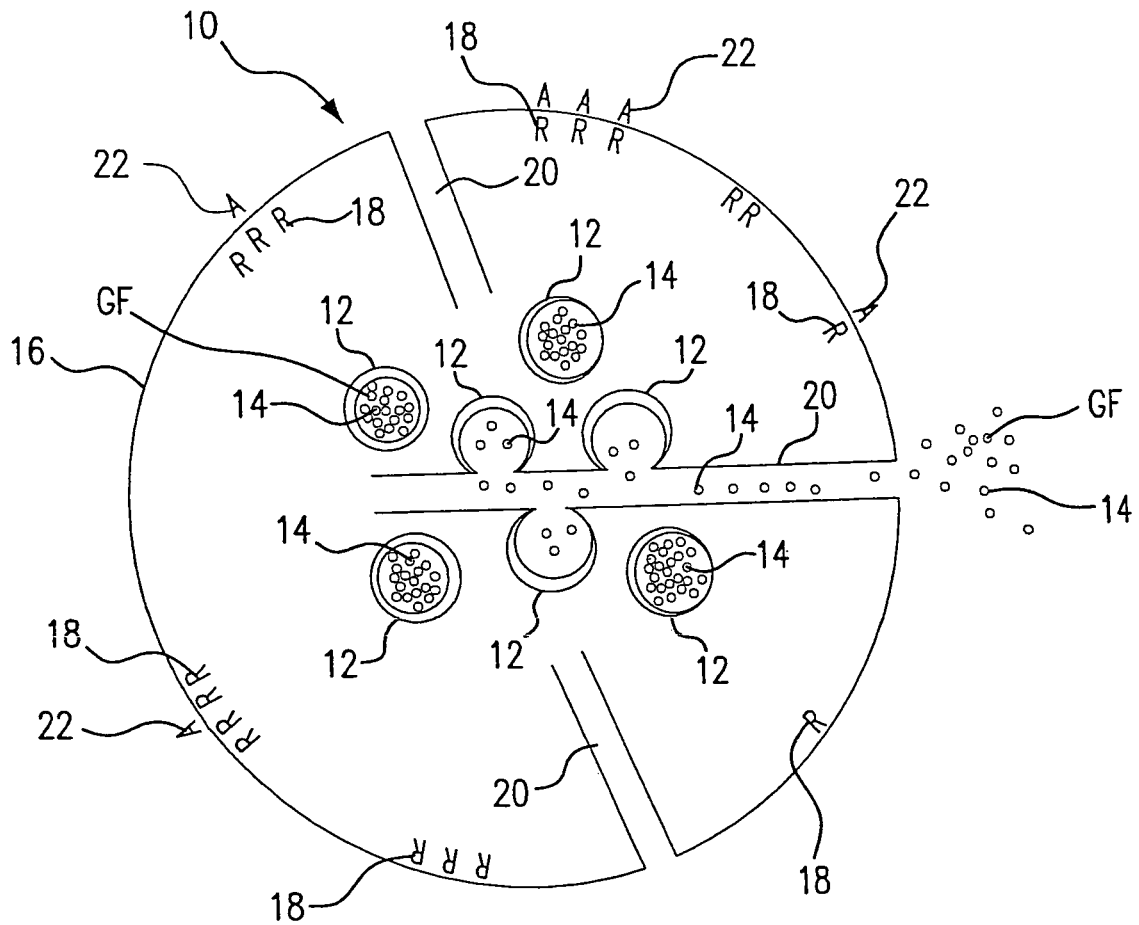
FIG. 2 is a schematic diagram of a platelet activated by an agonist, illustrating release of growth factors through the intracellular canal system of the platelet to the extracellular space of the plasma.

Referring to FIG. 2, there is schematically illustrated a platelet 10 when activated by an agonist 22 at the site of a cell membrane receptor 18. In the presence of an agonist the growth factors 14 are released from the alpha granules and may pass either through the internal dense tubular system into the open cannicular system 20 or pass directly into the open cannicular system 20. From the cannicular system 20, the released growth factors pass through openings in the platelet membrane 16 into the extracellular fluid surrounding the platelet. As further illustrated in FIG. 2, not all of the growth factors are released from the alpha granules in the presence of an activist 22. A number of alpha granules remain intact within the platelet to be released at a later time or not at all.

For improved clinical use of growth factors and to provide a diversified application of the growth factor composition of the present invention, it is important that the growth factor starting material not be frozen prior to separation of the growth factors from platelets. Preferably, the process should be performed above freezing temperatures, such as room temperature. In the preferred embodiment of the present invention, platelet rich plasma (PRP) is employed as the source of growth factors and may be obtained via methods known in the art.

Exemplary platelet plasma products are disclosed in U.S. Pat. Nos. 6,214,338; 6,010,627; 5,165,928; 6,303,112; and 6,649,072. The more concentrated the plasma is with platelets, the greater the concentration of growth factors that can be obtained via the present invention. The process for isolating growth factors from platelet rich plasma or other media containing platelet rich plasma is described hereinafter in greater detail.

As used herein, therapeutically effective amount of wound healing composition refers to the amount of the constituent bioactive elements or combinations thereof necessary to form a wound healing composition. The wound healing composition forms an extracellular matrix, proliferation of granulation tissue, facilitation of collagen laydown, vascular ingrowth, fibroblast proliferation, and stem cell activation, producing a reduction in the volume or surface area of a wound. All embodiments of the present invention are assumed to have minimal or greater therapeutically effective amount(s) of constituent substances or combinations thereof to possess the above positive bioactive properties.

Once the platelet rich plasma is obtained, it is placed under a vacuum, preferably under a sub-atmospheric or negative pressure. The PRP is in an unfrozen state, preferably at room temperature. Similarly, the vacuum is applied at above freezing and preferably at room temperature conditions. Optionally, whole blood or portions thereof, can be subjected to a controlled sub-atmospheric pressure under like conditions as described for PRP.

Sub-atmospheric pressure release can be artificially induced and controlled using devices with properties as described herein, which subject the platelet or growth factor starting material to a time oriented, specified range of sub-atmospheric pressure. Following the method described herein, the growth factor composition can be used on site or within a few days if kept cooled or further processed by lyophilization, referenced earlier, to store long term. The resulting composition of growth factors and bio-components obtained through this latter process retain normal bioactivity potential in a quiescent state until applied to target cells or tissues. Similarly, applying a controlled degree of sub-atmospheric pressure over a controlled period of time "in situ" will initiate the extraction/release of growth factors from platelets in the tissue(s) under the influence of negative pressure and results in a greater concentration of growth factor activity on the affected tissue(s).

In accordance with the present invention, the PRP is placed in one or more sterile vials and the vials placed in a vacuum chamber. A vacuum is applied using a conventional vacuum pump preferably at temperatures above freezing. In one example, it is applied between 1° C. and 37° C. and at a sub-atmospheric, negative pressure preferably between 5 millibars to 1 atmosphere. As a result of the application of the negative pressure, the growth factors are released into the surrounding nondestructive medium contained within the vials. Optionally, manual or electric driven devices can be substituted for the vacuum pump that generates a controlled, sustainable negative pressure on the blood or tissue sample for a defined period of time. An example device is a sealable container with a movable wall to confine the blood sample. The movable wall effectively allows for the chamber in the sealed container to expand without allowing for any exchange of air between the inside and outside of the container.

One device suitable for use for subjecting a patient's own growth factor starting material to sub-atmospheric pressure is disclosed in U.S. Pat. No. 8,871,745. This manually driven apparatus processes a known quantity of autologous growth factor starting material and subjects the material to a predetermined range of sub-atmospheric pressure. A built-in locking mechanism maintains a consistent pressure over a selected period of time. A growth factor composition is produced and extracted through a prepositioned withdrawal port. The growth factor composition is an extracellular fluid or plasma containing the released growth factors, such as the contents of platelet alpha, dense, and lambda granules that contain over 400 different bioactive proteins and biochemicals whose complex interactions in the healing process are not yet fully clarified, as well as components of the extracellular fluid or plasma. The extracellular fluid includes all body fluids outside of the cells, having two major components, interstitial fluid and blood plasma. Interstitial fluid is a solution that bathes and surrounds the cells of multicellular animals.

There is a direct inverted correlation of time versus negative pressure within the specified range of sub-atmospheric pressure. The shorter the length of time the negative pressure is applied, the greater the negative pressure must be. Conversely, the longer the length of time the negative pressure is applied, the less the negative pressure needs to be to release the growth factors from the platelets. A vacuum pressure source suitable for use in the process of the present invention is a rotary vane direct drive vacuum pump commercially available from Labconco Corporation of Kansas City, Mo. It should be understood that other commercially available vacuum generating devices are operable for use with the present invention.

As a result of the vacuum process, the growth factors are separated or released from the platelets in the growth factor starting material into the extracellular fluid containing plasma and water, leaving the platelets intact.

Figure 3:
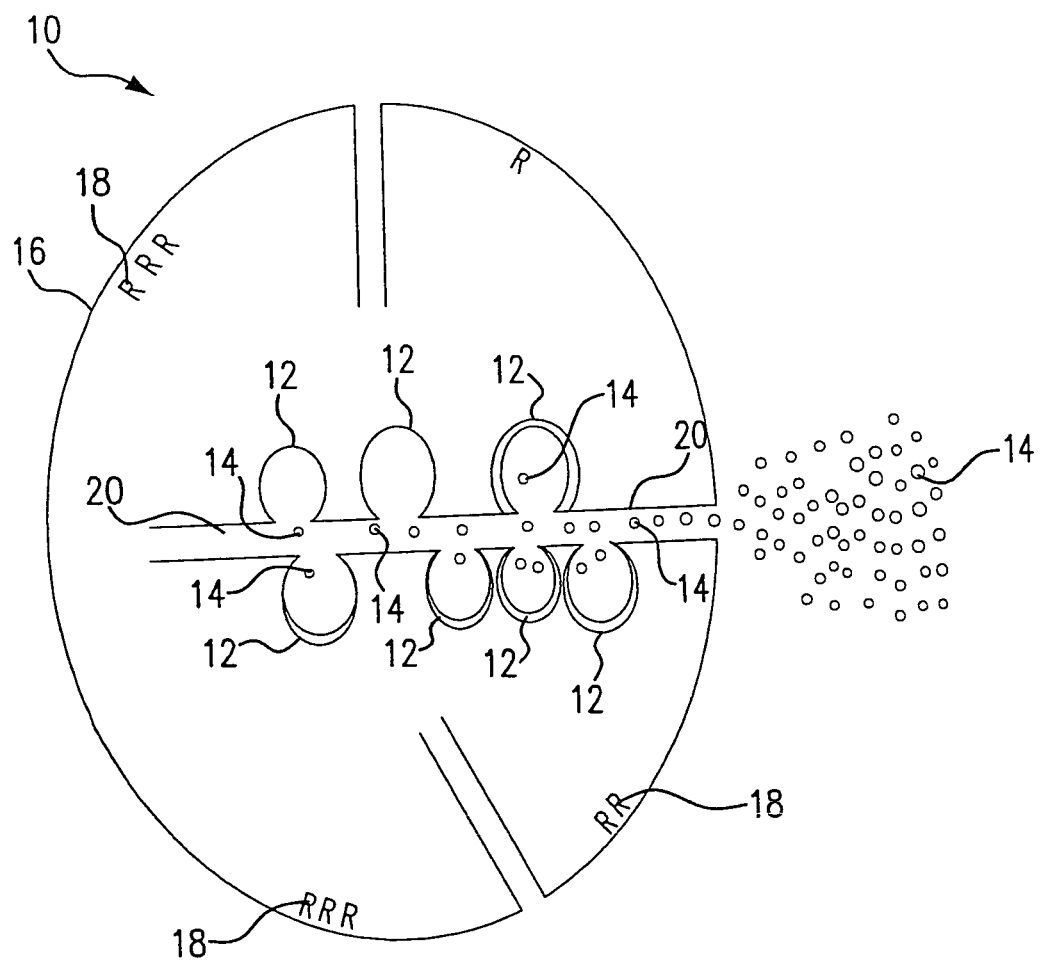
FIG. 3 is a schematic diagram of a platelet exposed to sub-atmospheric pressure, illustrating release of growth factors in the absence of an agonist through the intracellular canal system to the extracellular space of the plasma.

Now referring to FIG. 3, there is schematically illustrated the platelet 10 when exposed to sub-atmospheric pressure in accordance with the present invention. The sub-atmospheric pressure when applied to the platelet reduces the surface tension on the platelet membrane resulting in an increase in the opening of the cannicular system 20 through the platelet membrane 16. The sub-atmospheric pressure also creates an expansion of the dense tubular system resulting in expansion of the alpha granules and subsequent release of the growth factors. The growth factors released from the expanded granules pass from the dense tubular system into the open cannicular system 20.

As further illustrated in FIG. 3, in response to the sub-atmospheric pressure the alpha granules 12 migrate to the open cannicular system 20 so that the growth factors are removed from the alpha granules and pass into the cannicular system 20. Substantially all of the alpha granules are affected by the sub-atmospheric pressure to the extent that they are released from all of the alpha granules in the platelet and pass from the intracellular cannicular system 20 to the extracellular environment outside of the platelet. The movement of the extracted growth factors into the extracellular fluid (plasma) surrounding the platelet forms the growth factor composition, which is ready for wound healing and therapeutic application.

The plasma is a nondestructive medium, forming the growth factor composition. Plasma is the pale yellow liquid component of blood that normally holds the blood cells in whole blood in suspension. It makes up about 55% of the body's total blood volume. It is the intravascular fluid part of extracellular fluid and contains mostly water (95% by volume) and dissolved proteins (6-8% by volume). The growth factor composition can be concentrated by removing the water therein by a hemoconcentrating filter.

As shown in FIG. 3, the negative pressure created by the vacuum initiates movement of the growth factors out of the platelet granules surrounded by the platelet membrane and into the extracellular plasma. The extracted growth factors are collected for mixture with this non-destructive medium without dehydrating the growth factor starting material. The non-destructive medium forms with the growth factor starting material and the growth factor composition for application to wound healing or tissue regeneration. Ghost platelets may also remain for therapeutic use.

In one example of the process of the present invention, analysis of the vacuumed plasma using light microscopy and alpha granule staining techniques revealed intact platelets devoid of alpha granules (ghost platelets) in addition to the presence of platelet derived growth factors (PDGF) distributed in the plasma, as determined by lab assay. Platelet derived growth factors typically have a weight of 16-20 kDaltons. Specific growth factors extracted from the platelets in accordance with the present invention were measured to have an increased weight of 70-76 kDaltons. This is likely to be the result of a limited activation of growth factors allowing for the formation of a stable, larger protein moiety.

In another example, the process of the present invention for isolating growth factors is conducted using a composition of platelet rich plasma (PRP) and platelet poor plasma (PPP), as described in U.S. Pat. No. 6,649,072 ("the '072 patent"). The composition disclosed in the '072 patent is about a 3:1 ratio of PRP to PPP. With this ration of PRP to PPP, the amount of growth factors obtained includes platelet derived growth factor-AB/BB 356673.86 pg/ml, vascular endothelial growth factor 6440.667 pg/ml and platelet-derived epidermal growth factor 1106.73 pg/ml. This constitutes a significant recovery of growth factors not found in platelets that are released by the natural process of platelet activation and not otherwise attainable for positive clinical use in applying topically to a wound or injecting into soft tissue.

In another embodiment of the present invention, the growth factors are preserved for future bioactive use by preservation methods, such as lyophilization, cryopreservation, and flash drying. In this manner, a shelf-stable product is produced that is usable for years after preparation when stored at room temperature. When desired for use, the lyophilized product is reconstituted with sterile 0.9% normal saline solution. The lyophilized growth factors are also reconstituted using dionized water and bodily fluids. Suitable bodily fluids for reconstituting freeze-dried growth factors include plasma, hemoconcentrated plasma, whole blood, bone marrow aspirate, and combinations thereof.

The vacuum product, as above described, contains growth factors with or without platelets, leucocytes, or leucocyte-derived cytokines. The vacuumed product may be used immediately or lyophilized or freeze dried for future use. In accordance with another embodiment of the present invention, the vacuumed product is hemoconcentrated using a 0.2 micron filter to remove water. Prior to filtering and after the application of the sub-atmospheric pressure to the growth factor starting material, the vacuumed product is centrifuged to eliminate from the released growth factors the cellular components free of growth factors and the components of ghost platelets, bacteria, red blood cells, white blood cells, and other cellular debris, leaving behind the growth factor composition.

A preferred filter is one having a porosity of 0.2 microns or less. A suitable commercially available filter is the HPH Junior Hemoconcentrator sold by Minntech Therapeutic Technologies. Filtering the vacuumed and centrifuged product removes water to provide a growth factor composition of growth factor cytokines and plasma proteins. Centrifuging the vacuumed product separates the extracted growth factors, plasma proteins and water from the cellular debris, platelet membranes, ghost platelets, white blood cells, bacteria, and red blood cells. The centrifugation step is performed as disclosed in the '072 patent. It should be understood that the cellular debris cannot be completely separated from the growth factors without encountering a loss of growth factors.

Growth factors preserved as above described are reconstituted or hydrated in one method using sterile 0.9% normal saline solution. The preserved product is also reconstituted using deionized water, sterile water, other liquid media or bodily fluids including, but not limited to, plasma, hemoconcentrated plasma, whole blood, bone marrow aspirate, antibiotics or any combination thereof.

In another example of the present invention, 3 milliliters of the preserved product containing about 70% growth factors is reconstituted with about 3 milliliters of 0.9% normal saline or similar liquid media, as discussed above. For wound healing purposes, a therapeutically effective amount of the reconstituted product is applied topically to cover the wound. In another application, it is applied by injection at a location of soft tissue injury. Beyond wound healing, the fresh product and reconstituted product are useful in medical research applications as being supportive of growing tissues or culturing out stem cells. The reconstituted product may also be a liquid product containing protein-bound growth factors not previously lyophilized.

The growth factor composition serves as a precursor to the formation of an extracellular scaffold. The extracellular scaffold is a direct result from the formation of fibrin from fibrinogen. Fibrin is the fibrous, non-globular protein responsible for forming the extracellular scaffold. It is formed by the action of the protease thrombin on fibrinogen which causes the latter to polymerize. The polymerized fibrin forms the extracellular scaffold, a fibrin net, or hemostatic plug or clot which acts as net over a wound site. Factor XIII completes the "cross-linking" of the fibrin strands so that it hardens and contracts. The "cross-linked" fibrin forms a mesh or extracellular scaffold overlying the growth factor composition that completes the clotting cascade.

The growth factor composition includes fibrinogen in its current state. The extracellular scaffold is comprised of fibrin in its polymerized state. Once the growth factors are released from the platelets, they reside free in the plasma, creating the growth factor composition. The growth factor composition together with the extracellular scaffold forms the extracellular tissue matrix. The extracellular scaffold in addition to fibrin includes a collection of extracellular molecules secreted by cells. The extracellular matrix performs functions, such as cell and tissue adhesion, cell-to-cell communications and differentiation. The extracellular matrix also provides support, segregates tissues from one another and regulates intercellular communication. The extracellular matrix further functions to regulate a cell's (stem cell) dynamic behavior. The formation of the extracellular matrix is essential for regenerative processes like growth, wound healing and tissue formation and regeneration.

When the growth factors are released from the platelet granules into the extracellular fluid which is the plasma distinct from the extracellular matrix, the growth factors are "freed" from the cells but the cell remnants are still in the plasma or growth factor composition. The cells constitute the cellular debris, and the growth factors retain their distinct beneficial function.

Dependent upon the composition of the growth factor starting material, the released growth factor composition composed of growth factors and cytokines and the associated blood cell remnants or cellular debris resides in the extracellular fluid or plasma following the application of sub-atmospheric pressure. It is not critical to remove the cellular debris from the growth factor composition. The adhesion molecules remaining in the cellular debris further contribute to the formation of the extracellular scaffold. The extracellular tissue matrix composed of the extracellular scaffold and growth factor composition is instrumental in initiating and supporting the healing and tissue regenerative process.

Prior to preserving the isolated growth factors, in another embodiment various pharmaceutical agents are added to the composition. Preferably, these agents are antimicrobial agents which aid in the bioactivity of wound healing and in the treatment and prevention of infection. The antimicrobial agents include antibiotics, antiviral and antifungal agents, and the like. However, as known in the art, any number of other pharmaceutical agents may be employed. The quantity and type of agent selected must be compatible and stable in such products and be capable of withstanding lyophilization and other methods of preserving the growth factor product of the present invention.

In a further embodiment of the present invention, a bodily fluid, such as blood or an antibiotic, is used to reconstitute the final preserved product. This final product allows the clinician a wide berth of options on how it is used. In another example, by adding bone marrow aspirate and stem cells to the final product the patient achieves the benefits from both therapies. In a similar example, adding liposuction-derived tissue or surgically obtained adipose derived stem cells to the final product so that the patient achieves the benefits from both of these therapies. Additionally, the final product can be administered with an antibiotic solution at a specific anatomical site for wound healing and the like. Further, when the lyophilized final product and a thrombin solution are combined, a clot is initiated which is placed in a desired location to promote an effective seal and tissue growth.

The process and growth factor composition of the present invention are significant advancements in the field of using platelet based wound therapy agents. The process allows for the simple preparation of a product having one or more growth factors extracted and isolated from the growth factor starting material that may be subsequently lyophilized or preserved for bioactive use at a later date. The growth factors produced by the process of the present invention have demonstrated positive clinical signs in closing wounds and healing damaged soft tissue. In this manner large scale production of shelf-ready wound healing products is facilitated.

The process of the present invention of applying a sub-atmospheric pressure to a volume of growth factor starting material produces a growth factor composition suitable for a number of uses in wound healing, therapeutic, surgical, biomedical and cosmetic procedures, tissue regeneration and restoration, and providing bio-scaffold components and other essential resources to support living cells and tissues. The above applications of the present invention are illustrated in greater detail by the following examples, which should not be construed to limit the invention.

EXAMPLE 1

Figure 4:
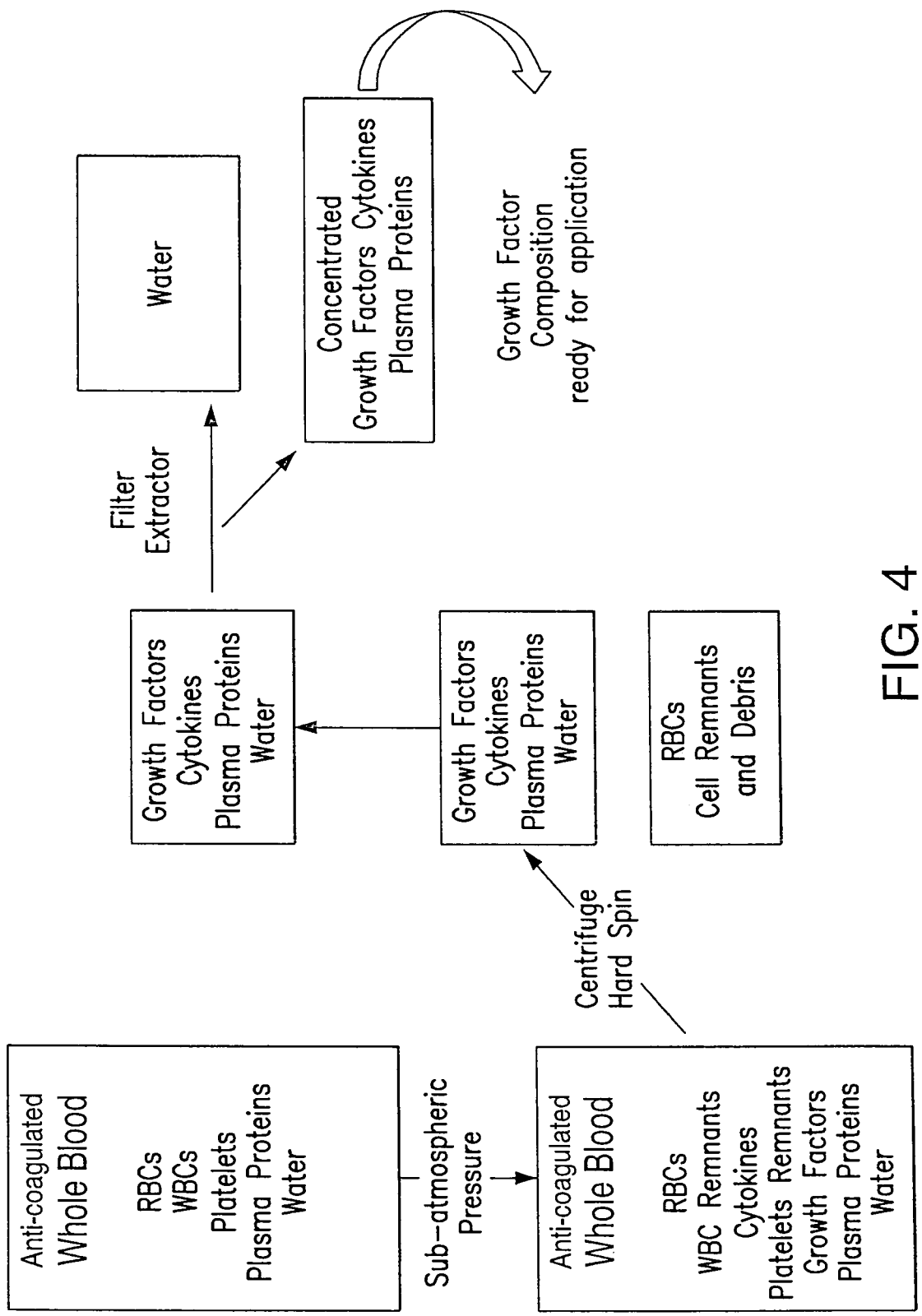
FIG. 4 is a diagrammatic flow chart of the process for releasing growth factors from platelets, illustrating the step of applying a hard centrifugal spin to the growth factors after release from platelets.

A wound healing composition was prepared aseptically (in a sterile manner), as diagrammatically illustrated in FIG. 4, by drawing a quantity of whole blood via conventional practice from a patient having a surface wound. The whole blood was collected in a vial and treated with an anticoagulant. At room temperature, the treated blood sample was placed in an airtight chamber. A pressure below atmospheric pressure was applied to the chamber by a vacuum pump supplied by Labconco Corporation. The sub-atmospheric pressure released the growth factors from the alpha granules in the platelets to pass through the open cannicular system of the platelets into the extracellular fluid outside the platelets. A vial of the extracellular fluid was placed in a conventional blood separation-type centrifuge and spun at about 5,000 to 6,000 rpm ("hard spin") to separate the growth factors, cytokines, plasma proteins and water from red blood cells, other cell remnants and cellular debris. The growth factors, cytokines, plasma proteins and water were removed from the vial via a syringe and introduced into a hemoconcentrator where the water is filtered out leaving a growth factor composition of concentrated growth factors, cytokines and plasma protein. The released growth factors were found to contain proteins of a weight in the range of 70-76 kDaltons. The released growth factors were applied topically to the area of a surface wound of the patient, and the wound healing was enhanced.

EXAMPLE 2

Figure 5:
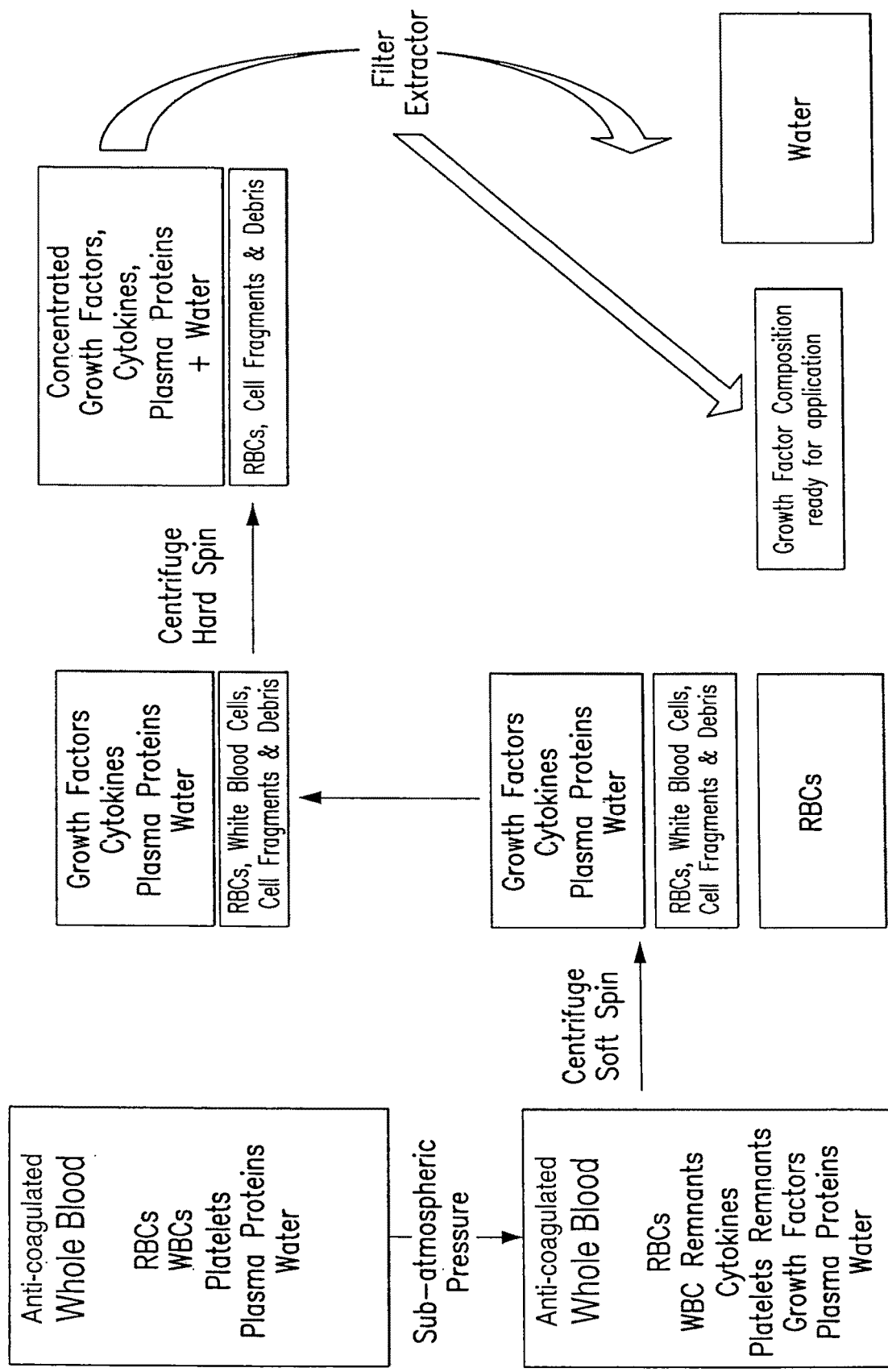
FIG. 5 is a diagrammatic flow chart similar to FIG. 4, illustrating the application of a soft centrifugal spin followed by a hard centrifugal spin to the released growth factors.

A wound healing composition was prepared, as diagrammatically illustrated in FIG. 5, by drawing a quantity of whole blood from a patient having a soft tissue wound in a tendon in accordance with Example 1 above. The anticoagulated whole blood was then subjected to negative pressure using a vacuum pump as set forth in Example 1 above to obtain the extracellular fluid containing growth factors. A vial of the extracellular fluid was then centrifuged at about 2,000 to 3,000 rpm ("soft spin") to separate the fluid into three layered components, as shown in FIG. 5. The first component included growth factors, cytokines, plasma proteins, and water. The second component included red blood cells, white blood cells and cell fragments and other debris. The third component or bottom layer was composed of packed red blood cells. The first and second components are removed from packed red blood cells and subjected to a hard centrifugal spin, as described above in Example 1. Thereafter, the product of the hard spin is filtered via a hemoconcentrator, as also described above, to remove the water and provide a growth factor composition ready for application. The growth factor composition was then injected into a soft tissue wound of the patient. The injection of growth factors enhanced healing of the wound.

EXAMPLE 3

Figure 6:
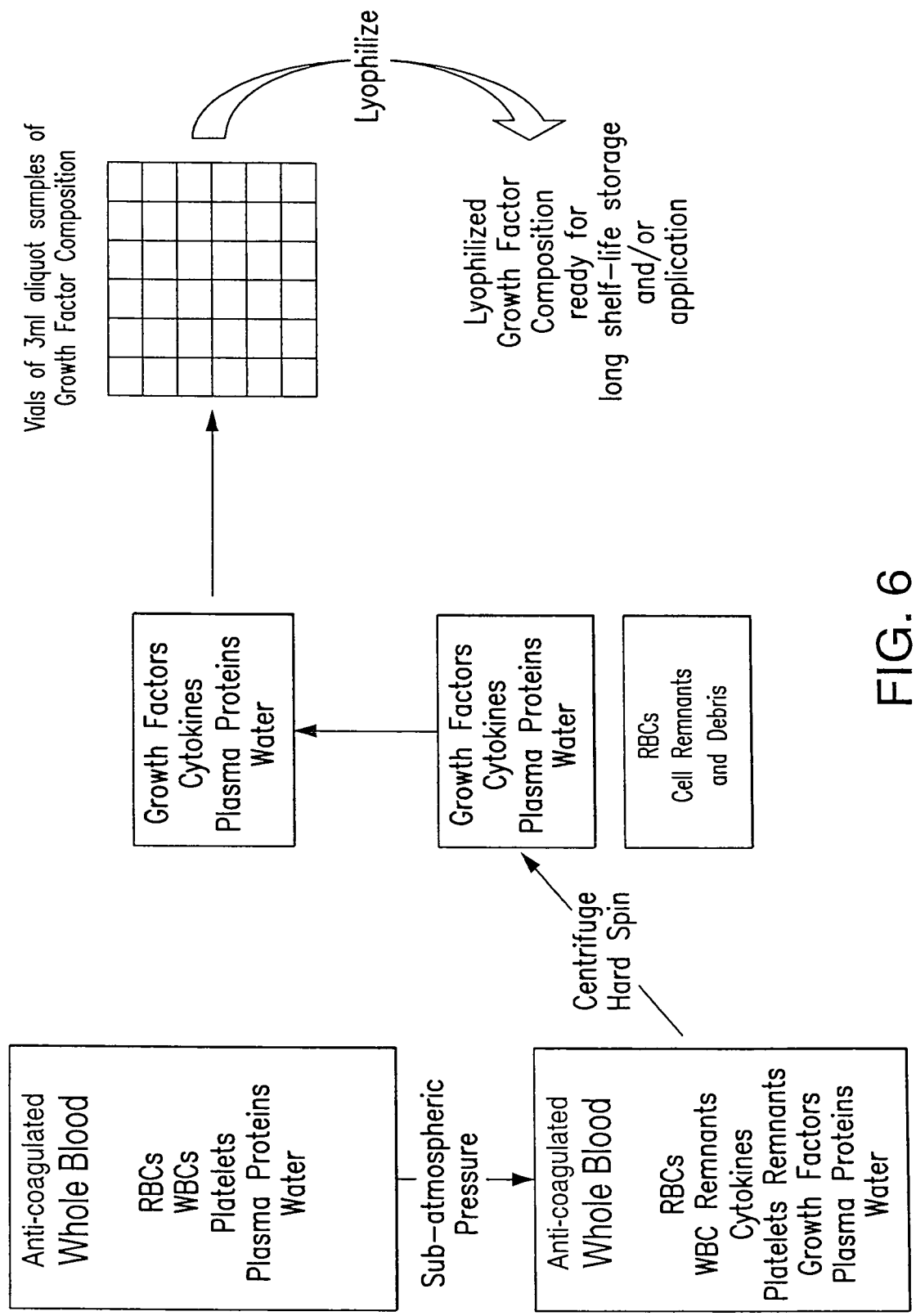
FIG. 6 is a diagrammatic flow chart similar to FIGS. 4 and 5, illustrating the step of lyophilizing the growth factors after being released from the platelets and subjected to a hard centrifugal spin.

A wound healing composition was prepared as diagrammatically illustrated in FIG. 6 from a healthy individual not having a wound by drawing a quantity of whole blood in accordance with Example 1 above. An anticoagulant was added to the blood. Growth factors were released from the whole blood by performing the method steps described in Example 1 above. After a hard spin as performed in Example 1, the growth factor composition was removed from the layer of packed red blood cells and cellular debris. The unfiltered growth factor composition was then divided into a plurality of individual equal volumes, such as vials of 3 ml. liquid samples shown in FIG. 6. Each square shown in FIG. 6 represents an individual vial of growth factor composition ready for use or storage. The collection of samples was lyophilized in a conventional manner to provide a preserved, shelf-stable product. After a preselected period of time after lyophilization, two sample vials of preserved growth factors were reconstituted or hydrated by mixing the preserved growth factors with a sterile 0.9% normal saline solution. One quantity of the reconstituted growth factors was applied topically to the area of a surface wound of one patient. The second quantity of the reconstituted growth factors was injected into a soft tissue wound of a second patient. In each patient the wound healing took place in an enhanced manner.

The wound healing compositions prepared in accordance with the present invention are not limited to the uses disclosed in Examples 1-3 above. Filtered and unfiltered growth factors prepared by the process of the present invention have many other uses. Some additional examples (not all inclusive) include the treatment of injuries to tendons and ligaments, bone and joint healing, oral and maxillofacial surgery, hair generation and stem cell recruitment, skin rejuvenation, and application with stem cells to create a three dimensional organ bio-scaffold to be seeded with progenitor cells.

The application of a sub-atmospheric pressure to tissues is not limited to growth factor starting materials. The application of sub-atmospheric pressure has been demonstrated to significantly reduce or eliminate the normal cellular structure of processed whole blood and blood cells. The process can be applied to animal tissues composed of cells to eliminate intact cell structures throughout, leaving behind an acellular tissue matrix. The tissue matrix is washed with one or more sterile biocompatible solution(s) to remove devitalized, diseased or pathologic compromised tissue cells, bacteria, undesirable cellular debris or components retaining antigenicity. Clearing of such tissue of its cellular components facilitates application of a growth factor composition described herein along with stem cell reseeding of the acellular tissue matrix in an in vitro environment supportive of stem cell activity. Such a process using the products produced by the application of sub-atmospheric pressure promotes autologous, allogeneic, or xenogeneic sourced organ regeneration for potential transplantation.

By using a selected one of the methods described in Examples 1, 2, or 3 above, applications of growth factor compositions are applied by injection, spray infusion or topically where appropriate. The growth factor compositions are applied to traumatized tissues of human, canine and or equine subjects affected with muscle-skeletal injuries and joint conditions, autoimmune disorders, respiratory tract conditions, ocular conditions, neurologic trauma and disease related pathology. Treatment of dermal thermal burns and dental related procedures are enhanced and accelerated by application of growth factor compositions prepared in accordance with the present invention. The growth factor composition is also used in the treatment of diseased tissue including immune mediated diseases, such as alopecia areata, inflammatory diseases such as multiple sclerosis and COPD, degenerative diseases and procedures used in hair reproduction and organ growth for transplantation.

Due to multiple factors, including age and diurnal fluctuations in platelet counts, benefits in individual tissue responses vary. Although very unlikely, risks associated with autologous use of growth factor compositions are limited to contaminants or additional trauma introduced during the application process. Allogeneic or xenogeneic growth factor compositions may additionally result in protein related allergenic reactions due to individual patient sensitivity. The transfer of certain microorganisms, such as a virus, can be potentially eliminated by prescreening of donors.

According to the provisions of the patent statutes, we have explained the principle, preferred construction and mode of operation of our invention and have illustrated and described what we now consider to represent its best embodiments. However, it should be understood that within the scope of the appended claims the invention may be practiced otherwise than as specifically illustrated and described.

We claim:

1. A wound healing and tissue regenerative composition comprising,
    unfrozen growth factor starting material including platelet granules obtained from the tissue of a subject,
    growth factors extracted from the platelet granules by applying a preselected sub-atmospheric pressure to said unfrozen growth factor starting material,
    said extracted growth factors remaining in an inactivated state,
    said extracted growth factors being centrifuged to separate the cellular structure of said growth factor starting material from said extracted growth factors without activating the extracted growth factors, and
    said extracted growth factors mixed with a nondestructive medium in a bioactive state to generate a positive reaction on living tissue to enhance tissue growth.

2. A wound healing and tissue regenerative composition as set forth in claim 1 in which,
    said growth factors consisting of essentially platelet-derived epidermal growth factor, platelet factor 4, transforming growth factor beta acidic fibroblast growth factor, basic fibroblast growth factor, transforming growth factor A, insulin-like growth factors 1 and 2, B thromboglobulin-related proteins, thrombospondin, fibronectin, von Willibrand's factor, fibropeptide A, fibrinogen, albumin, plasminogen activator inhibitor 1, osteonectin, regulated upon activation normal cell expressed and presumably secreted, grow-A, vitronectin, fibran D-dimer, factor V, antithrombin III, immunoglobulin-G, immunoglobulin-M, immunoglobulin-A, a2-macroglobluin, aniogenin, Fg-D, elasstase, keratinocyte growth factor, epidermal growth factor tumor necrosis factor, fibroblast growth factor and interleukin-1, keratinocyte growth factor-2, and combinations thereof.

3. A wound healing composition as set forth in claim 1 in which,
    said growth factor starting material is selected from the group consisting essentially of platelets, platelet rich plasma, whole blood, bone marrow, umbilical cord fluid, adipose tissue, vascular tissues and combinations thereof.

4. A wound healing and tissue regenerative composition set forth in claim 1 in which,
    said extracted growth factors including growth factors having a molecular weight in the range of 70-76 kDaltons.

5. A wound healing and tissue regenerative composition as set forth in claim 1 in which,
    said growth factor starting material includes platelet rich plasma.

6. A wound healing and tissue regenerative composition as set forth in claim 5 in which,
    said platelet rich plasma is in an unfrozen state.

7. A wound healing and tissue regenerative composition as set forth in claim 1 in which,
    said extracted growth factors include a therapeutically effective amount of bioactive proteins and biochemical materials to promote wound healing and tissue regeneration.

8. A wound healing and tissue regenerative composition as set forth in claim 1 in which,
    said wound healing composition forms an extracellular tissue matrix, vascular ingrowth, stem cell activation, fibroblast proliferation, proliferation of granulation tissue, and facilitation of collagen laydown all resulting in a reduction in the surface area of a wound.

9. A wound healing and tissue regenerative composition as set forth in claim 1 in which,
    said growth factors are released from platelets in said growth factor starting material into the plasma external of the platelets.

10. A wound healing and tissue regenerative composition as set forth in claim 1 which includes,
    a growth factor composition containing said growth factors released from platelets in said growth factor starting material, and
    said growth factor composition mixed with a nondestructive medium external of said platelets.

11. A wound healing and tissue regenerative composition as set forth in claim 1 in which,
    said growth factor composition is free of red blood cells and white blood cells.

12. A wound healing and tissue regenerative composition as set forth in claim 1 in which,
    said extracted growth factors include compatible pharmaceutical agents to promote wound healing.

13. A wound healing composition as set forth in claim 12 in which,
    said pharmaceutical agents include antimicrobial agents selected from the group consisting essentially of antibiotics, antiviral and antifungal agents.

* * * * *